US009017388B2

(12) United States Patent
Molz, IV

(10) Patent No.: US 9,017,388 B2
(45) Date of Patent: Apr. 28, 2015

(54) METHODS FOR CORRECTING SPINAL DEFORMITIES

(75) Inventor: Fred J. Molz, IV, Birmingham, AL (US)

(73) Assignee: Warsaw Orthopedic, Inc., Warsaw, IN (US)

(*) Notice: Subject to any disclaimer, the term of this patent is extended or adjusted under 35 U.S.C. 154(b) by 2283 days.

(21) Appl. No.: 11/531,705

(22) Filed: Sep. 14, 2006

(65) Prior Publication Data
US 2008/0097433 A1    Apr. 24, 2008

(51) Int. Cl.
A61B 17/88 (2006.01)
A61B 17/70 (2006.01)
A61B 17/02 (2006.01)

(52) U.S. Cl.
CPC .......... A61B 17/8866 (2013.01); A61B 17/7067 (2013.01); A61B 17/7062 (2013.01); A61B 17/707 (2013.01); A61B 17/7077 (2013.01); A61B 2017/0256 (2013.01)

(58) Field of Classification Search
USPC .................................. 606/279, 248, 264, 263
See application file for complete search history.

(56) References Cited

U.S. PATENT DOCUMENTS

| | | | |
|---|---|---|---|
| 4,003,376 A | 1/1977 | McKay et al. | |
| 4,773,402 A * | 9/1988 | Asher et al. | 606/250 |
| 4,848,328 A | 7/1989 | Laboureau et al. | |
| 5,034,011 A | 7/1991 | Howland | |
| 5,053,038 A | 10/1991 | Sheehan | |
| 5,290,289 A | 3/1994 | Sanders et al. | |
| 5,496,318 A * | 3/1996 | Howland et al. | 606/249 |
| 5,593,408 A | 1/1997 | Gayet et al. | |
| 5,700,292 A | 12/1997 | Margulies | |
| 5,853,414 A | 12/1998 | Groiso | |
| 5,893,889 A * | 4/1999 | Harrington | 623/17.16 |
| 6,127,597 A | 10/2000 | Beyar et al. | |
| 6,132,464 A * | 10/2000 | Martin | 623/17.15 |
| 6,146,421 A * | 11/2000 | Gordon et al. | 623/17.15 |
| 6,248,110 B1 * | 6/2001 | Reiley et al. | 606/93 |
| 6,287,308 B1 | 9/2001 | Betz et al. | |
| 6,296,643 B1 | 10/2001 | Hopf et al. | |
| 6,299,613 B1 | 10/2001 | Ogilvie et al. | |
| 6,325,805 B1 | 12/2001 | Ogilvie et al. | |
| 6,610,091 B1 | 8/2003 | Reiley | |
| 6,616,669 B2 | 9/2003 | Ogilvie et al. | |
| 6,623,484 B2 | 9/2003 | Betz et al. | |
| 6,746,450 B1 | 6/2004 | Wall et al. | |
| 6,835,205 B2 | 12/2004 | Atkinson et al. | |
| 6,837,904 B2 | 1/2005 | Ralph et al. | |
| 6,899,713 B2 * | 5/2005 | Shaolian et al. | 606/262 |

(Continued)

FOREIGN PATENT DOCUMENTS

WO    WO 95/02372       1/1995
WO    WO 2005/074825 A1 8/2005

OTHER PUBLICATIONS

Gruca, Adam, The Pathogenesis and Treatment of Idiopathic Scoliosis: A Preliminary Report, 1958; 40:570-584, The Journal of Bone and Joint Surgery, United States.

Primary Examiner — Ellen C Hammond

(57) ABSTRACT

The present application is directed to devices and methods for correcting a spinal deformity. A spacer is positioned between processes that extend outward from a pair of vertebral members. A force applicator is operatively connected to apply a force to the vertebral members. The spacer then acts as a fulcrum with the force causing the vertebral members to pivot about the spacer and become aligned in a more desired orientation to eliminate or reduce the deformity.

11 Claims, 8 Drawing Sheets

(56) References Cited

U.S. PATENT DOCUMENTS

| | | |
|---|---|---|
| 6,966,911 B2 | 11/2005 | Groiso |
| 6,972,019 B2 * | 12/2005 | Michelson ................. 606/86 A |
| 6,974,478 B2 | 12/2005 | Reiley et al. |
| 7,052,497 B2 | 5/2006 | Sherman et al. |
| 7,074,239 B1 | 7/2006 | Cornwall et al. |
| 7,077,865 B2 * | 7/2006 | Bao et al. ................... 623/17.12 |
| 7,125,410 B2 * | 10/2006 | Freudiger .................... 606/254 |
| 7,204,837 B2 * | 4/2007 | Paul ............................ 606/276 |
| 7,445,637 B2 * | 11/2008 | Taylor ........................ 623/17.16 |
| 7,578,849 B2 * | 8/2009 | Trieu ......................... 623/17.15 |
| 7,585,316 B2 * | 9/2009 | Trieu ............................ 606/279 |
| 7,588,592 B2 * | 9/2009 | Winslow et al. ............. 606/249 |
| 7,635,377 B2 * | 12/2009 | Zucherman et al. .......... 606/249 |
| 7,635,378 B2 * | 12/2009 | Zucherman et al. .......... 606/249 |
| 7,666,209 B2 * | 2/2010 | Zucherman et al. .......... 606/249 |
| 7,682,376 B2 * | 3/2010 | Trieu ............................ 606/248 |
| 7,691,130 B2 * | 4/2010 | Bruneau et al. ............... 606/249 |
| 8,419,772 B2 * | 4/2013 | Thompson et al. ........... 606/254 |
| 2002/0151895 A1 | 10/2002 | Soboleski et al. |
| 2003/0023241 A1 | 1/2003 | Drewry et al. |
| 2003/0088251 A1 | 5/2003 | Braun et al. |
| 2003/0220643 A1 * | 11/2003 | Ferree .............................. 606/61 |
| 2004/0034351 A1 | 2/2004 | Sherman et al. |
| 2004/0102774 A1 | 5/2004 | Trieu |
| 2004/0243239 A1 * | 12/2004 | Taylor ........................ 623/17.13 |
| 2005/0021035 A1 | 1/2005 | Groiso |
| 2005/0055096 A1 * | 3/2005 | Serhan et al. .............. 623/17.11 |
| 2005/0171539 A1 | 8/2005 | Braun et al. |
| 2005/0216004 A1 | 9/2005 | Schwab |
| 2005/0245929 A1 * | 11/2005 | Winslow et al. ............... 606/61 |
| 2006/0058790 A1 * | 3/2006 | Carl et al. ....................... 606/61 |
| 2006/0100709 A1 | 5/2006 | Reiley |
| 2007/0093834 A1 * | 4/2007 | Stevens et al. ................. 606/69 |
| 2007/0173820 A1 * | 7/2007 | Trieu .............................. 606/61 |
| 2007/0173821 A1 * | 7/2007 | Trieu .............................. 606/61 |
| 2007/0173935 A1 * | 7/2007 | O'Neil et al. .............. 623/17.11 |
| 2010/0106190 A1 * | 4/2010 | Linares ........................ 606/249 |

* cited by examiner

METHODS FOR CORRECTING SPINAL DEFORMITIES

BACKGROUND

The present application is directed to methods for correcting spinal deformities and, more particularly, to methods that apply a corrective force to one or more of the vertebral members.

The spine is divided into four regions comprising the cervical, thoracic, lumbar, and sacrococcygeal regions. The cervical region includes the top seven vertebral members identified as C1-C7. The thoracic region includes the next twelve vertebral members identified as T1-T12. The lumbar region includes five vertebral members L1-L5. The sacrococcygeal region includes nine fused vertebral members that form the sacrum and the coccyx. The vertebral members of the spine are aligned in a curved configuration that includes a cervical curve, thoracic curve, and lumbosacral curve. Intervertebral discs are positioned between the vertebral members and permit flexion, extension, lateral bending, and rotation.

Various deformities may affect the normal alignment and curvature of the vertebral members. Scoliosis is one example of a deformity of the spine in the coronal plane, in the form of an abnormal curvature. While a normal spine presents essentially a straight line in the coronal plane, a scoliotic spine can present various lateral curvatures in the coronal plane. The types of scoliotic deformities include thoracic, thoracolumbar, lumbar or can constitute a double curve in both the thoracic and lumbar regions. Schuermann's kyphosis is another example of a spinal deformity that affects the normal alignment of the vertebral members.

SUMMARY

The present application discloses methods for treating a spinal deformity. One method includes inserting a spacer between adjacent first and second vertebral members. A force applicator is then operatively connected to the vertebral members to apply a corrective force. The positioning of the spacer and the force applicator may vary depending upon the context of use. The applicator applies a force that causes the vertebral members to pivot about the spacer and become aligned to reduce the spinal deformity.

DETAILED DESCRIPTION

Figure 1:
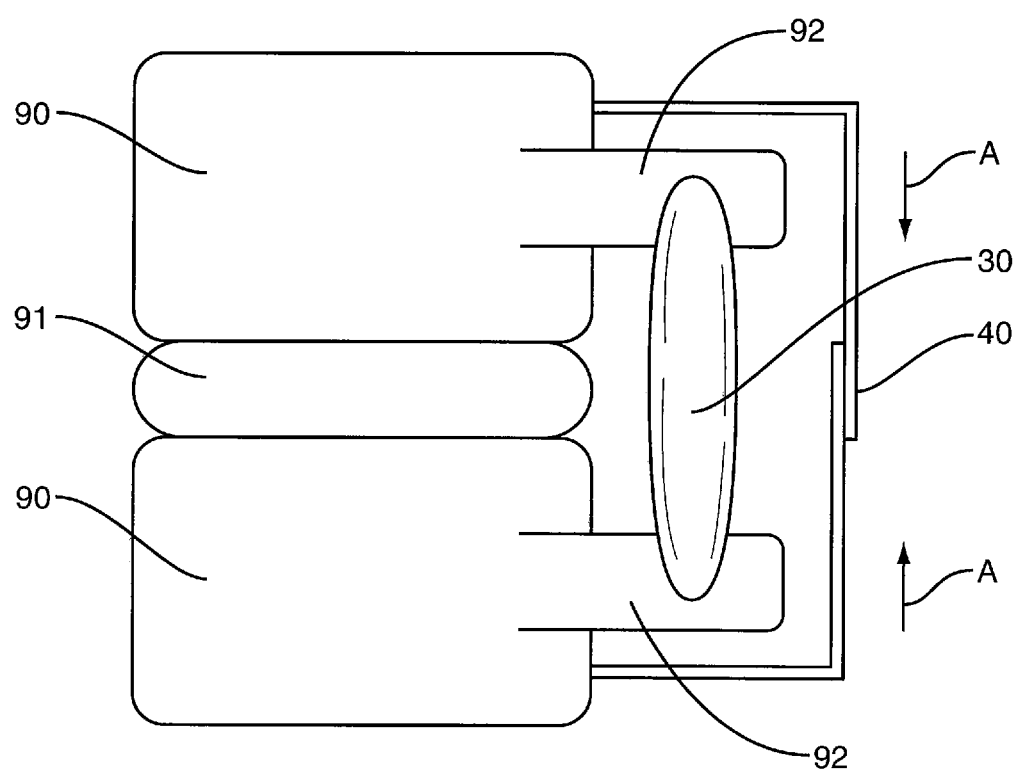
FIG. 1 is schematic coronal view of a device positioned relative to a pair of vertebral members according to one embodiment.

The present application is directed to methods for correcting a spinal deformity. FIG. 1 illustrates a pair of vertebral members 90 and an intervertebral disc 91. A spacer 30 is positioned between processes 92 that extend outward from the vertebral members 90. A force applicator 40 is operatively connected to each of the vertebral members 90 to apply a compressive force as illustrated by arrows A to the vertebral members 90. The spacer 30 acts as a fulcrum with the compressive force causing the vertebral members 90 to pivot about the spacer 30. The spacer 30 also maintains the foraminal space while the force applicator 40 provides curve correction to eliminate or reduce the deformity.

Figure 2:
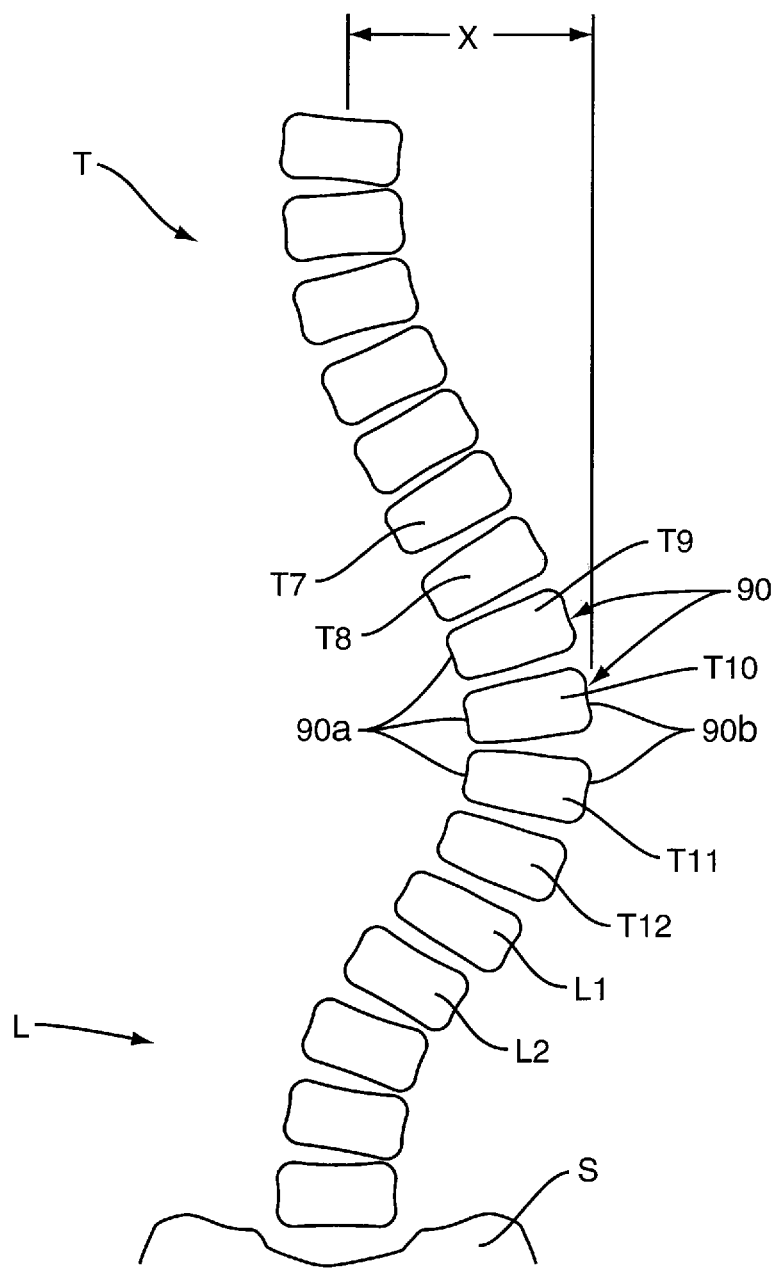
FIG. 2 is schematic coronal view of an example of a scoliotic spine.

FIG. 2 illustrates a patient's spine that includes a portion of the thoracic region T, the lumbar region L, and the sacrum S. This spine has a scoliotic curve with an apex of the curve being offset a distance X from its correct alignment in the coronal plane. The spine is deformed laterally so that the axes of the vertebral members 90 are displaced from the sagittal plane passing through a centerline of the patient. In the area of the lateral deformity, each of the vertebral members 90 includes a concave side 90a and a convex side 90b. One embodiment of the devices and methods position a fulcrum 30 on the convex side 90b of two or more adjacent vertebral members 90. A compressive force is applied to the convex side 90b of the vertebral members 90 to reduce and/or eliminate the spinal deformity. In one embodiment, a distractive force is applied to the concave side 90a to reduce and/or eliminate the spinal deformity.

Figure 3:
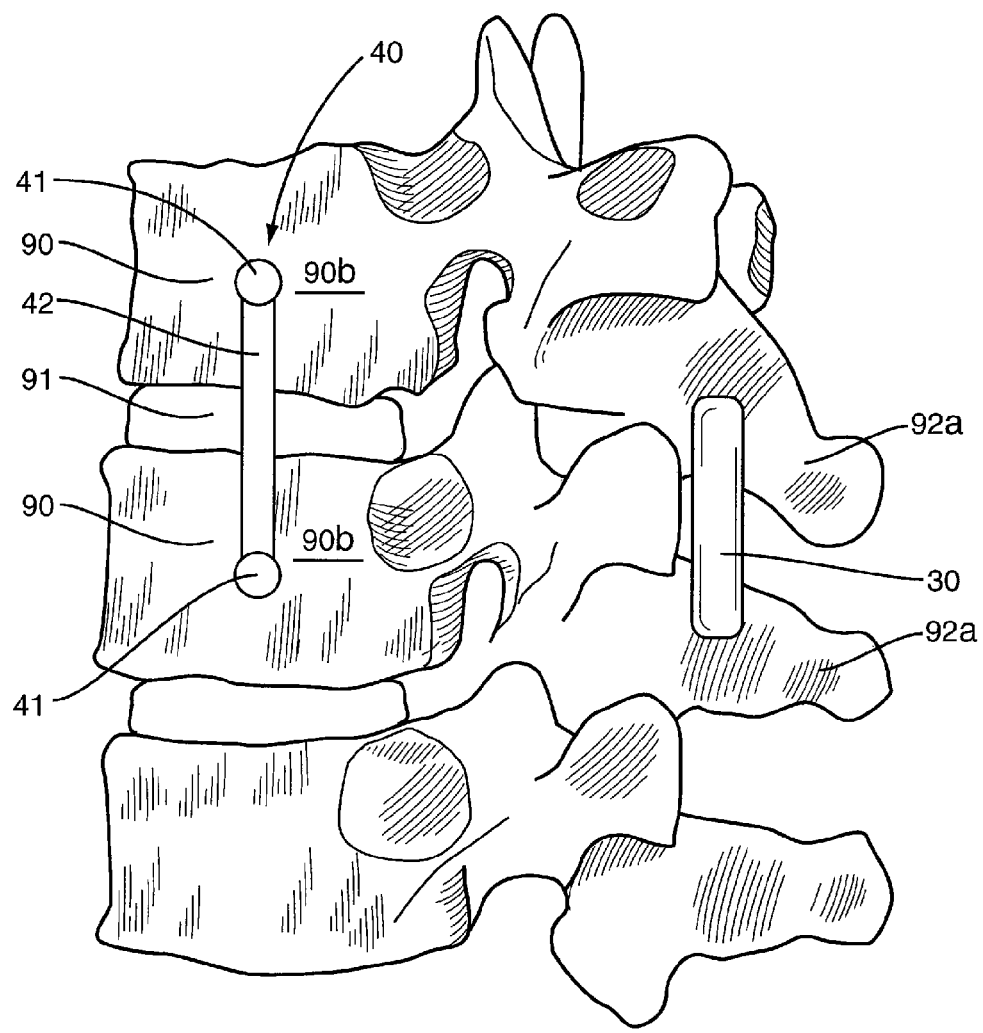
FIG. 3 is schematic sagittal view of a spacer and a force applicator mounted to vertebral members according to one embodiment.

FIG. 3 illustrates one embodiment that corrects the spinal deformity. A spacer 30 is positioned between the spinous processes 92a that extend outward from the posterior of each of the vertebral members 90. The force applicator 40 is attached to the convex side 90b of the vertebral members 90. The force applicator 40 applies a corrective force to the vertebral members 90 to provide curve correction. Spacer 30 is used as a fulcrum for the vertebral members 90 and also maintains the foraminal space. The spacer 30 and force applicator 40 may be effective in patients with remaining skeletal growth.

Spacer 30 also acts as a positioning device to reduce the load placed onto specific areas of the vertebral members 90. Prior art methods have included tethering that place an abnormally large load on the facet joints. This may cause the facet joints to experience excessive wear resulting in damage to the vertebral members 90, and/or pain to the patient. Spacer 30 absorbs all or a part of the load to reduce and/or eliminate wear on the facet joints and pain to the patient.

Figure 4:
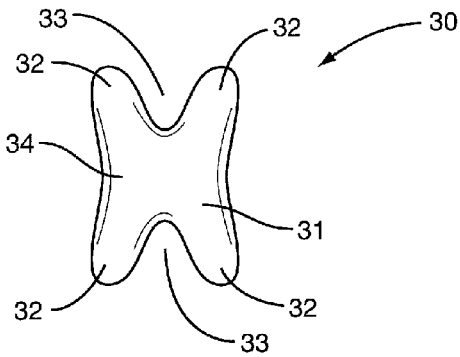
FIG. 4 is a side view of a spacer according to one embodiment.
Figure 5:
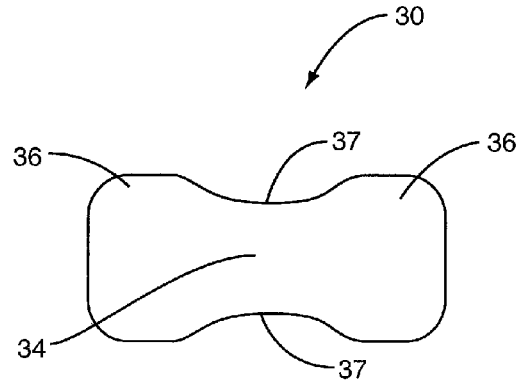
FIG. 5 is a side view of a spacer according to one embodiment.
Figure 6:
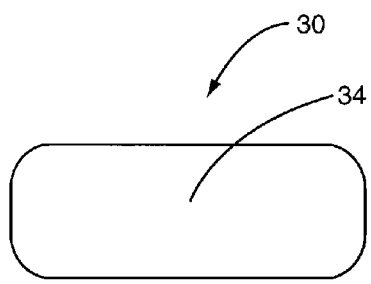
FIG. 6 is side view of a spacer according to one embodiment.
Figure 7:
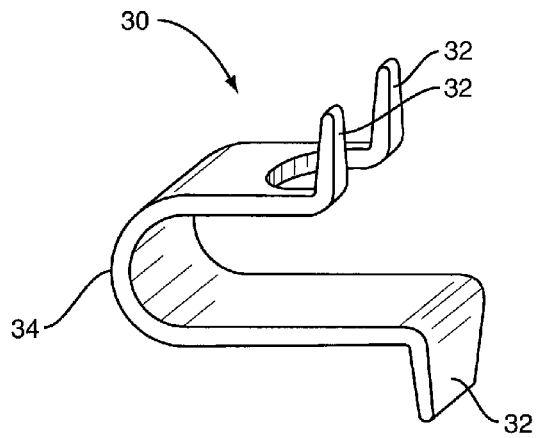
FIG. 7 is perspective view of a spacer according to one embodiment.

Spacer 30 may include a variety of shapes and sizes. FIG. 4 illustrates an embodiment with a central section 34 with superior and inferior arms 32 that are spaced apart with a gap 33 formed therebetween. The spacer 30 is positioned with the processes 92 positioned within each of the gaps 33 and being separated by the central section 34. The arms 32 extend along the lateral sides of each of the processes 92 to maintain the attachment. FIG. 5 illustrates another embodiment of a spacer 30 with enlarged lateral end sections 36 forming inferior and superior indents 37 to receive the spinous processes 92a. The central section 34 formed between the indents 37 separates the spinous processes 92a. FIG. 6 illustrates an embodiment with a central section 34 sized to space the spinous processes 92a. FIG. 7 includes an offset central section 34 with inferior and superior arms 32 positioned to contact the spinous processes 92a.

The spacer 30 may be formed for a variety of biocompatible polymeric materials, including elastic materials, such as plastics, metals, elastomeric materials, hydrogels or other hydrophilic-polymers, or composites thereof. The nature of the materials employed to form the spacer 30 may be selected to exhibit a sufficient stiffness to space apart the spinous processes 92a. The term stiffness is used to refer to the resistance of an elastic body to deflection by an applied force.

The spacer 30 may also be fully or partially constructed from bio-absorbable material. Bio-absorbable material provides the positioning and/or stiffness functions for a limited time after the spacer 30 is implanted and is then eventually absorbed by the body. In one embodiment, the bio-absorbable material is gradually absorbed by the body. During this initial period, the body may heal to an extent that the spacer 30 is adequate to support the vertebral members 90 and/or the body is able to position the spacer 30. In one embodiment, the bio-absorbable material is replaced with tissue, such as fibrous tissue and fibrous scar tissue. The bio-absorbable material may be formed from a wide variety of natural or synthetic materials including fibrin, albumin, collagen, elastin, silk and other proteins, polyethylene oxide, cyanoacrylate, polylactic acid, polyester, polyglycolic acid, polypropylene fumarate, tyrosine-based polycarbonate and combinations thereof. Other suitable materials include demineralized bone matrix. In one embodiment, bio-absorbable material may be a woven fabric.

Various embodiments of spacers 30 are disclosed in U.S. patent application Ser. Nos. 11/341,233 and 11/341,200 each filed Jan. 27, 2006 and each entitled "Interspinous Devices and Methods of Use". These applications are hereby incorporated by reference. Another embodiment of a spacer is the DIAM Spinal Stabilization System available from Medtronic Sofamor Danek of Memphis, Tenn., also hereby incorporated by reference.

In one embodiment, the force applicator 40 applies a compressive force to the convex side 90b of the vertebral members 90. FIG. 3 illustrates one embodiment of the force applicator 40 that includes an anchor 41 mounted within each of the vertebral members 90. A tether 42 extends between and is operatively connected to each anchor 41. Anchors 41 include a shaft that mounts within the vertebral member, and a head that extends outward beyond the vertebral member 90. The anchors 41 can be made from a variety of biocompatible materials, including synthetic or natural autograft, allograft or xenograft tissues, and can be resorbable or non-resorbable nature. Examples of tissue materials include hard tissues, connective tissues, demineralized bone matrix and combinations thereof. Further examples of resorbable materials are polylactide, polyglycolide, tyrosine-derived polycarbonate, polyanhydride, polyorthoester, polyphosphazene, calcium phosphate, hydroxyapatite, bioactive glass, and combinations thereof. Further examples of non-resorbable materials are carbon-reinforced polymer composites, shape-memory alloys, titanium, titanium alloys, cobalt chrome alloys, stainless steel, ceramics and combinations thereof. Each of the anchors 41 may be substantially the same, or different in both size, shape, and materials.

Figure 8:
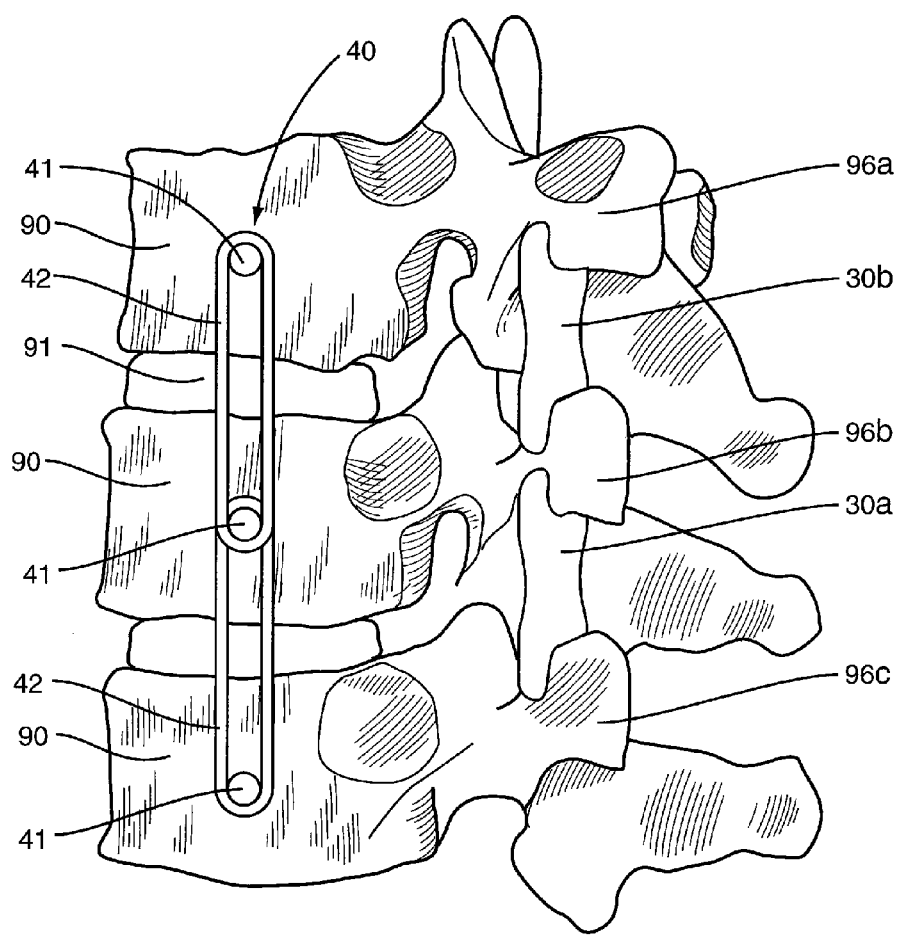
FIG. 8 is a schematic sagittal view of spacers and tethers positioned relative to vertebral members according to one embodiment.

Various types of tethers 42 may be used to apply the force. FIG. 3 illustrates a rod that connects with and extends between the anchors 41. A first end of the rod is connected to the superior anchor 41, and a second end is connected to the inferior anchor 41. FIG. 8 illustrates another embodiment with cables 42 that extend between the anchors 41. Other embodiments may include, but are not limited to, staples, cables, artificial strands, rods, plates, springs, artificial ligaments, and combinations thereof. The tethers 42 may be rigid, semi-rigid, flexible, partially flexible, resorbable, non-resorbable, superelastic, or include shape-memory material. Further examples of tether constructs include those that are single strand, multiple strands, braided, or combinations thereof.

In some embodiments, the tether 42 is constrained to the anchors 41. Other embodiments may include the tether 42 being unconstrained or semi-constrained connections. Still other embodiments may include connections that are combinations of the above. An example of a semi-constrained connection is a ball joint that allows at least some range of articulation of the construct relative to the anchor, or float within a neutral zone. Examples of constrained or semi-constrained connections include a construct that is wrapped around, crimped, clamped or penetrated by a portion of the anchor or a set screw or cap engageable to the anchor. Such constrained connections fix the construct to the anchor so that there is no or minimal relative movement therebetween Tether material can include but is not limited to polymers, such as polyester and polyethylene; superelastic metals, such as nitinol; shape memory alloy, such as nickel titanium; resorbable synthetic materials, such as suture material, metals, such as stainless steel and titanium; synthetic materials, allograft material; and bioelastomer material. U.S. Patent Application Publication 2003/0088251 discloses various types of anchors and tethers and is herein incorporated by reference.

The spacer 30 may be positioned at different locations relative to the vertebral members 90. In the embodiment of FIG. 3, spacer 30 is positioned between the spinous processes 92a. In another embodiment, the spacer 30 is positioned between the transverse processes 96 as illustrated in FIG. 8. FIG. 8 specifically illustrates an embodiment with two separate spacers 30a, 30b positioned between the transverse processes 96a, 96b, 96c of three separate vertebral members 90. In another embodiment (not illustrated), a first spacer is positioned between the transverse processes, and a second spacer is positioned between the spinous processes.

Figure 11:
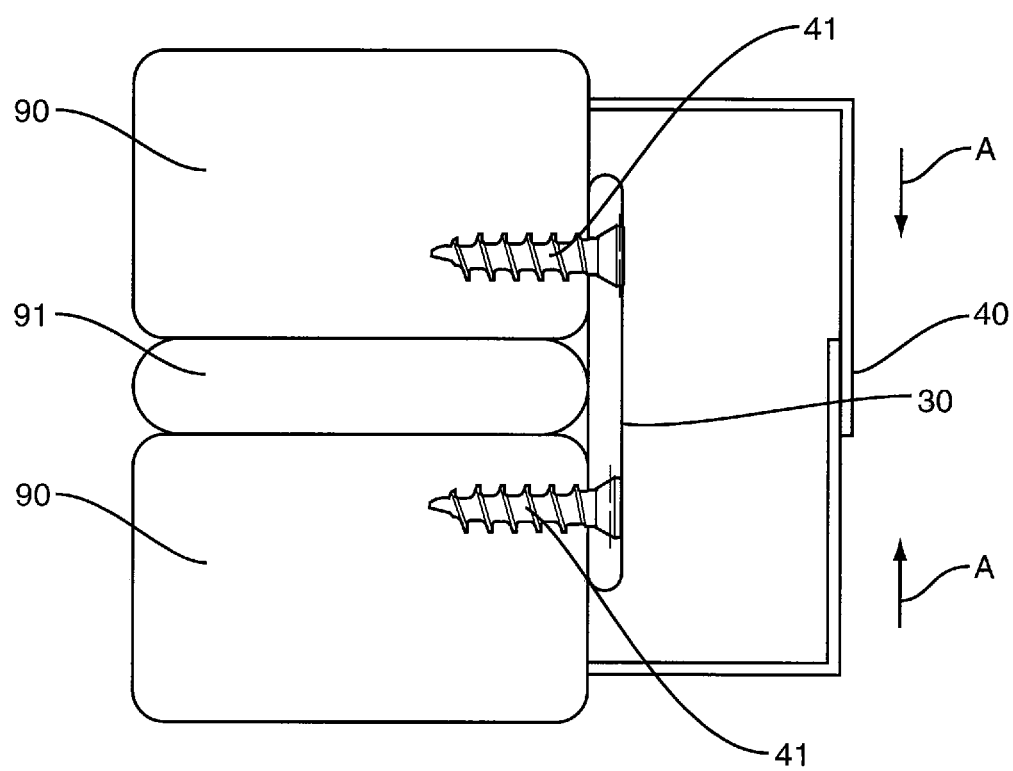
FIG. 11 is a schematic coronal view of a device positioned relative to a pair of vertebral members according to one embodiment.

FIG. 11 illustrates another embodiment with the spacer 30 attached to the vertebral members 90 with anchors 41. A first surface of the spacer 30 is placed against the vertebral members 90 with a second surface facing outward. One or more anchors 41 may attach the spacer 30 to each vertebral member 90. The force applicator 40 applies a force to the vertebral members 90 causing them to pivot about the spacer 30. This positioning allows for the spacer 30 to act as a fulcrum at other positions than between the spinous processes 92 and transverse processes 96.

Some embodiments include a single spacer 30. This usually occurs when the tether 42 extends between two adjacent vertebral members 90. FIG. 3 illustrates an example of a single spacer 30. Other embodiments feature multiple spacers 30 such as FIG. 8. Multiple spacers 30 may be required when a tether 42 or combination of tethers 42 extends to three or more vertebral members 90. In some embodiments, two or more force applicators 40 are attached to the vertebral members 90.

In the embodiment illustrated in FIG. 3, the force applicator 40 is attached to the convex side 90b of the vertebral members 90. The force applicator 40 applies a compressive force to the convex side 90b to arrest or at least minimize growth on the convex or "long" side 90b of the spine, thereby allowing the concave or "short" side 90a of the spine to grow and catch up with the long side. In another embodiment, force applicator 40 is attached to the concave side 90a and applies a distractive force to the vertebral members 90. This distractive force causes the vertebral members 30 to move about the spacer 30. In distractive force applications, the spacer 30 may be positioned on an opposite side of the vertebral member 90 from the force applicator 40. By way of example, a spacer 30 is positioned on the convex side 90b when a force applicator 40 is attached to and applies a distractive force to the concave side 90a.

In one embodiment, a single force applicator 40 and spacer 30 are attached to a single level of the spine, such as at the apex of the deformity. Using FIG. 2 as an example, the force applicator 40 and spacer 30 may span between the T9-T10 vertebral members 90. Alternatively, additional applicators 40 and/or spacers 30 may further span to the adjacent vertebral members 90 which in this example include T8 and T11. In other embodiments, force applicators 40 and spacers 30 may be used at multiple levels of the spine. By way of example, a first applicator 40 and spacer 30 may span between T10-T11, with a second applicator 40 and spacer 30 spanning T12-L1.

It should be understood that the spinal deformity depicted in FIG. 2 is but one of many types of spinal deformities that can be addressed by the devices and techniques of the present application. Most commonly the devices and methods are expected to be used for either primary thoracic or thoracolumbar curves. They can be used for correction of the thoracic curve as an isolated curve, or the lumbar curve as an isolated curve. The devices may further be used in combination with the shortening of the opposite side of the vertebral member 90.

Figure 9:
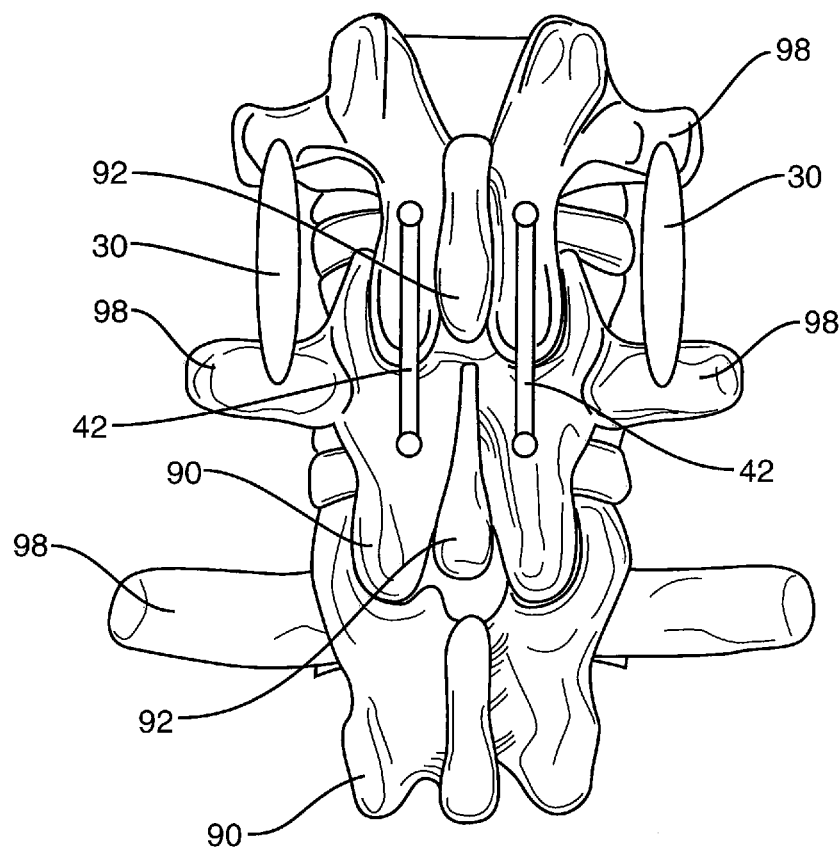
FIG. 9 is a schematic coronal view of spacers and tethers positioned relative to vertebral members according to one embodiment.
Figure 10:
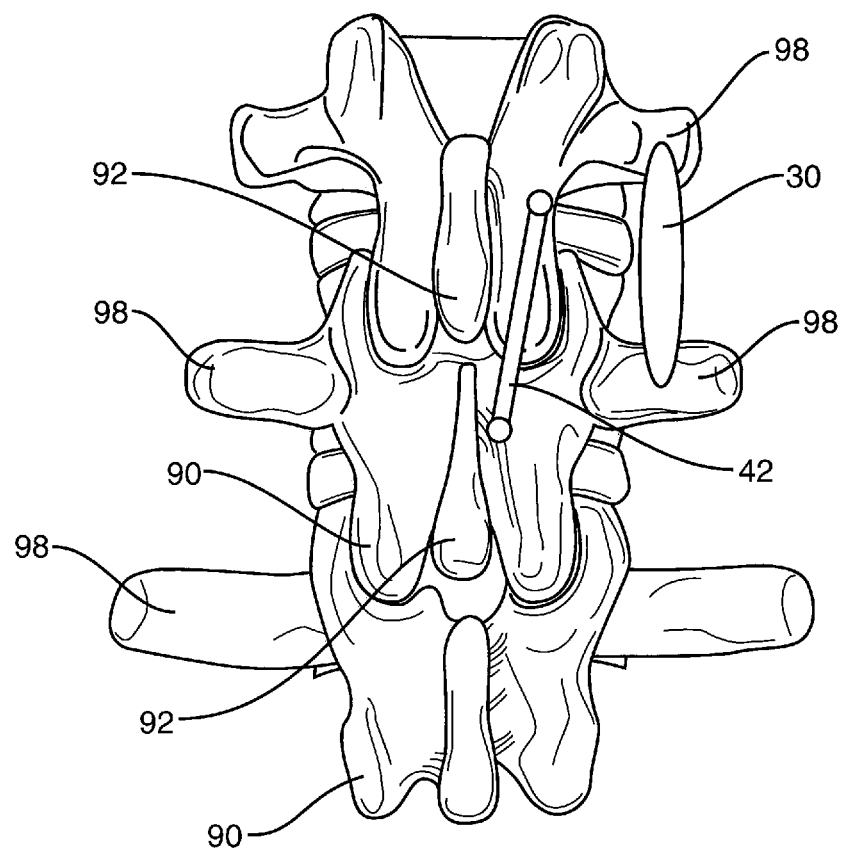
FIG. 10 is a schematic coronal view of a spacer and tether positioned relative to vertebral members according to one embodiment.

The devices and methods may be used to treat spinal deformities in the coronal plane, such as a scoliotic spine illustrated in FIG. 2. The devices and methods may also be used to treat deformities in the sagittal plane, such as a kyphotic spine or Scheurmann's kyphosis. FIGS. 9 and 10 illustrate embodiments for treating such deformities. One or more tethers 42 are attached to a posterior section of the vertebral members 90. The tethers 42 may extend across two or more of the vertebral members 90 depending upon the context of use. One or more spacers 30 are positioned between the vertebral members 90. In some embodiments, spacers 30 are positioned between the transverse processes 98. The spacer or spacers 30 may relieve some of the force applied to the facet joints. In addition, a spacer 30 may be positioned between the spinous processes 92 (not illustrated). In another embodiment, one or more tethers 42 are positioned on the posterior of the vertebral members 90 without use of a spacer 30.

One embodiment includes accessing the spine from an anterior approach. Other applications contemplate other approaches, including posterior, postero-lateral, antero-lateral and lateral approaches to the spine, and accessing various regions of the spine, including the cervical, thoracic, lumbar and/or sacral regions.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. The force applicator 40 may apply a force to arrest or minimize growth of the convex side 90b of the vertebral members 90, or alternatively, to simply prevent further deformity of the spine. The present embodiments are, therefore, to be considered in all respects as illustrative and not restrictive, and all changes coming within the meaning and equivalency range of the appended claims are intended to be embraced therein.

What is claimed is:

1. A method of treating a spinal deformity comprising the steps of:
    inserting a spacer between processes of adjacent first and second vertebral members such that the processes are each disposed in a gap defined by arms of the spacer and the arms each engage lateral sides of one of the processes;
    attaching a force applicator to an exterior of a convex and lateral side of the vertebral members with the force applicator extending across an intervertebral space formed between the vertebral members; and
    applying a compressive force via the force applicator and causing the vertebral members to move about the spacer and treat the spinal deformity.

2. The method of claim 1, wherein the step of inserting the spacer between processes of adjacent vertebral members comprises inserting the spacer between transverse processes.

3. The method of claim 1, wherein the step of inserting the spacer between processes of adjacent vertebral members comprises inserting the spacer between spinous processes.

4. The method of claim 1, further comprising pivoting the vertebral members and deforming the spacer.

5. The method of claim 1, wherein the step of applying the compressive force via the force applicator further causes the vertebral members to pivot about the spacer and correct the spinal deformity.

6. The method of claim 1, further comprising attaching a second force applicator and a second spacer at a second spinal level and applying a second force and further reducing the spinal deformity.

7. The method of claim 1, further comprising inserting a second spacer between second processes of the adjacent first and second vertebral members.

8. The method of claim 1, wherein the gaps are each concave and are continuously curved.

9. A method of treating a deformed spine having a lateral deformity, the spine including first and second vertebral members along the deformity each having a concave side and a convex side, the method comprising the steps of:
    inserting a spacer between processes of the first vertebral member and the second vertebral member such that the processes are each disposed in a gap defined by arms of the spacer and the arms each engage lateral sides of one of the processes;
    attaching an elongated force applicator to lateral sides of the first and second vertebral members with a first section of the force applicator attached to the first vertebral member and a second section of the force applicator attached to the second vertebral member, the force applicator extending across an intervertebral space formed between the first and second vertebral members; and applying a compressive force through the force applicator and causing the first and second vertebral members to move about the spacer and treat the lateral deformity.

10. The method of claim 9, wherein attaching the elongated force applicator to the lateral sides of the first and second vertebral members comprises attaching the force applicator to a convex side of the first and second vertebral members.

11. A method of treating a spinal deformity comprising the steps of:
   inserting a spacer between processes of adjacent first and second vertebral members;
   attaching a force applicator to an exterior of a convex and lateral side of the vertebral members with the force applicator extending across an intervertebral space formed between the vertebral members;
   pivoting the vertebral members and deforming the spacer; and
   applying a compressive force via the force applicator and causing the vertebral members to move about the spacer and treat the spinal deformity.

* * * * *